United States Patent [19]

Itaya et al.

[11] Patent Number: 5,770,767

[45] Date of Patent: Jun. 23, 1998

[54] PROCESS FOR PRODUCING 2-FLUOROCYCLOPROPANECARBOXLIC ACID

[75] Inventors: Nobushige Itaya, Nishinomiya; Ryuhei Wakita; Asako Kubo, both of Toyonaka; Mikio Sasaki, Ibaraki; Takashi Namba, Matsubara; Yusuke Yukimoto, Chiba, all of Japan

[73] Assignees: Sumitomo Chemical Company Limited., Osaka-Fu; Daiichi Pharmaceutical Co., Ltd., Tokyo-To, both of Japan

[21] Appl. No.: 593,940

[22] Filed: Jan. 30, 1996

[30] Foreign Application Priority Data

Jan. 31, 1995 [JP] Japan .................................... 7-014578
Jan. 31, 1995 [JP] Japan .................................... 7-014580

[51] Int. Cl.⁶ .................................................. C07C 61/04
[52] U.S. Cl. ............................................................. 562/506
[58] Field of Search ............................................. 562/506

[56] References Cited

U.S. PATENT DOCUMENTS 5,081,283  1/1992  Gassen et al. .

FOREIGN PATENT DOCUMENTS 0665140  3/1994  Japan .
0797353  4/1995  Japan .

OTHER PUBLICATIONS

J. Flourine Chem. 1990, 49, P127–139, Gassen et al., Flourinated Cyclopropanecarboxylic Acids and Their Derivatives.

*Primary Examiner*—Michael L. Shippen
*Attorney, Agent, or Firm*—Sughrue, Mion, Zinn, Macpeak & Seas, PLLC

[57]  ABSTRACT

A process for producing a 2-fluorocyclopropane-carboxylic acid of formula [I]

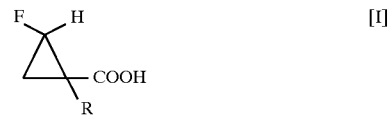

by reducing a 2-halo-2-fluorocyclopropanecarboxylic acid of formula [II]

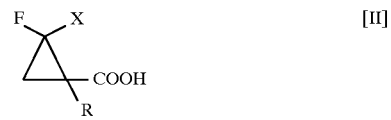

the reduction being carried out by developing a Raney nickel alloy in the presence of the 2-halo-2-fluorocyclopropanecarboxylic acid of formula [II], or by contacting the 2-halo-2-fluorocyclopropanecarboxylic acid of formula [II] with hydrogen in an aqueous solvent using a Raney nickel catalyst.

13 Claims, No Drawings

PROCESS FOR PRODUCING 2-FLUOROCYCLOPROPANECARBOXLIC ACID

FIELD OF THE INVENTION

The present invention relates to a process for producing a 2-fluorocyclopropanecarboxylic acid represented by formula [I]

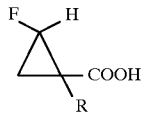

wherein R is a hydrogen atom or a lower alkyl group.

BACKGROUND OF THE INVENTION

2-Fluorocyclopropanecarboxylic acids are compounds known as intermediates for medicines, agricultural chemicals and the like (Japanese Unexamined Patent Publications No. 78644/1990, No. 65140/1994 and No. 231475/1990). It is also known that the 2-fluorocyclopropanecarboxylic acids are produced, for example, by reducing a 2-halo-2-fluorocyclopropanecarboxylic acid using a Raney nickel catalyst in an ethanol solvent under pressure of hydrogen (Journal of Fluorine Chemistry, 49, 127 (1990)).

However, the known process involves problems such as very low yields of the desired product.

SUMMARY OF THE INVENTION

The present inventors conducted extensive research on the process for reducing the 2-halo-2-fluorocyclopropanecarboxylic acid of formula [II] to solve the above industrial problems, and found that the desired 2-fluorocyclopropanecarboxylic acid of formula [I] can be easily produced in a high yield by the simple procedure of developing a Raney nickel alloy in the presence of the 2-halo-2-fluorocyclopropanecarboxylic acid of formula [II] without feeding hydrogen. Process (i) of the present invention has been accomplished based on this novel finding and further research.

Moreover, as a result of extensive research on the process for reducing the 2-halo-2-fluorocyclopropanecarboxylic acid of formula [II] using a Raney nickel catalyst, the present inventors surprisingly found that when using water as a reaction solvent, the desired 2-fluorocyclopropanecarboxylic acids of formula [I] can be produced in a remarkably improved yield. Process (ii) of the present invention has been accomplished based on this novel finding and further research.

Thus, the present invention provides a process for producing a 2-fluorocyclopropanecarboxylic acid represented by formula [I]

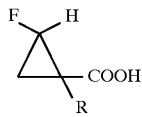

wherein R is a hydrogen atom or a lower alkyl group comprising subjecting to reduction a 2-halo-2-fluorocyclopropanecarboxylic acid represented by formula [II]

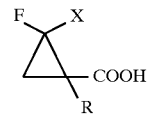

wherein R is as defined above and X is a chlorine atom, a bromine atom or an iodine atom, the reduction being carried out by (i) developing a Raney nickel alloy in the presence of the 2-halo-2-fluorocyclopropanecarboxylic acid represented by formula [II], or (ii) contacting the 2-halo-2-fluorocyclopropanecarboxylic acid represented by formula [II] with hydrogen in an aqueous solvent using a Raney nickel catalyst.

DETAILED DESCRIPTION OF THE INVENTION

Substituent R in the 2-halo-2-fluorocyclopropanecarboxylic acid of formula [II] for use as a starting material in the present invention include, for example, a hydrogen atom or a lower alkyl group, such as methyl, ethyl, propyl, butyl, pentyl and the like. Examples of the lower alkyl group are preferably alkyl groups having 1 to 5 carbon atoms, more preferably alkyl groups having 1 to 2 carbon atoms.

Substituent X is, for example, a chlorine atom, a bromine atom or an iodine atom, among which a chlorine atom is usually employed.

The fluorine atom and carboxyl group on the cyclopropane ring may be either cis or trans configuration.

Specific examples of the 2-halo-2-fluorocyclopropanecarboxylic acid of formula [II] include 2-chloro-2-fluorocyclopropanecarboxylic acid, 2-bromo-2-fluorocyclopropanecarboxylic acid, 2-iodo-2-fluorocyclopropanecarboxylic acid, 2-chloro-2-fluoro-1-methylcyclopropanecarboxylic acid, 2-bromo-2-fluoro-1-methylcyclopropanecarboxylic acid, 2-iodo-2-fluoro-1-methylcyclopropanecarboxylic acid, 2-chloro-2-fluoro-1-ethylcyclopropanecarboxylic acid, 2-chloro-2-fluoro-1-propylcyclopropanecarboxylic acid and the like.

The 2-halo-2-fluorocyclopropanecarboxylic acid of formula [II] can be easily prepared by conventional methods, for example, by the method disclosed in Japanese Unexamined Patent Publication No. 9499/1994 wherein a 2-halo-2-fluorocyclopropanecarboxylic acid ester is prepared from a 1-halo-1-fluoroethylene and a diazoacetic acid ester, and then hydrolyzed. Alternatively, the 2-halo-2-fluorocyclopropanecarboxylic acid of formula [II] can be prepared by the method disclosed in the abovementioned Journal of Fluorine Chemistry, 49, 127 (1990) wherein a 2-halo-2-fluoro-1-vinylcyclopropane is prepared from a butadiene and a dihalofluoromethane, and then oxidized with potassium permanganate or the like.

Process (i)

Process (i) of the invention is now described in detail wherein the reduction is carried out by developing a Raney nickel alloy in the presence of the 2-halo-2-fluorocyclopropanecarboxylic acid of formula [II].

Process (i) of the present invention is characterized in that the Raney nickel alloy is developed in the presence of the 2-halo-2-fluorocyclopropanecarboxylic acid of formula [II]. Said carboxylic acid of formula [II] is usually used in the form of an inorganic salt such as sodium salt, potassium salt or the like, but of course may be used in the form of a free acid.

The Raney nickel alloy comprises nickel and aluminum. The nickel content thereof is usually about 30 to 60% by weight, preferably about 40 to 50% by weight. The Raney nickel alloy is used in an amount of usually about 0.05 to 5 parts by weight, preferably about 0.1 to 1 part by weight, per part by weight of the 2-halo-2-fluorocyclopropanecarboxylic acid of formula [II], and is usually used in the form of a powder.

Development of the Raney nickel alloy (i.e., the procedure of leaching aluminum from the Raney nickel alloy using an inorganic base) is usually carried out by allowing an inorganic base to act on the alloy in the presence of a solvent.

As the solvent, water is usually used. The solvent may also be a mixture of water and alcohols such as lower alcohols, in particular alcohols having 1 to 3 carbon atoms (e.g., methanol, ethanol and the like). Water or the mixed solvent of water and the alcohol is usually used in an amount of about 2 to 50 parts by weight, preferably about 2 to 20 parts by weight, per part by weight of the Raney nickel alloy.

Usable inorganic bases include, for example, alkali metal hydroxides such as sodium hydroxide, potassium hydroxide and the like. The inorganic base is usually used in the form of an aqueous solution. The concentration of the aqueous solution of the inorganic base can be suitably selected from a wide range, but is usually about 10 to 50% by weight, preferably about 15 to 35% by weight. The amount of the inorganic base is usually about 0.1 to 40 parts by weight, preferably about 0.5 to 20 parts by weight, per part by weight of the Raney nickel alloy.

The reaction can be accelerated by using at least one base selected from the group consisting of ammonia and organic bases, in combination with the inorganic base. Examples of the organic base include lower alkylamines, particularly mono- or di-alkylamines having 1 to 3 carbon atoms, such as methylamine, dimethylamine, ethylamine and the like, lower amino alcohols, particularly aminoalcohols having 1 to 3 carbon atoms, such as ethanolamine, i-propanolamine and the like, lower alkylenediamines, particularly alkylenediamines having 1 to 3 carbon atoms, such as ethylenediamine and the like, and mixtures of these amines.

When using a lower alkylenediamine, it is preferable to conjointly use ammonia and/or a monoamine such as the lower alkylamine, the lower amino alcohol and the like, whereby leaching of nickel caused by the use of the lower alkylenediamine is inhibited, and the degree of coloring of the effluent due to nickel ion is reduced.

When using the lower alkylenediamine in combination with ammonia and/or the monoamine such as the lower alkylamine, the lower amino alcohol or the like, the molar ratio of ammonia and/or the monoamine to the lower alkylenediamine is not specifically limited, but ammonia and/or the monoamine is usually used in an amount effective for suppressing the leaching of nickel. Generally, it is preferable to use about 10 to 300 moles of at least one member selected from the group consisting of ammonia and the monoamine, per mole of the lower alkylenediamine.

The amount of the base(s) selected from the group consisting of ammonia and organic bases is usually about 15 moles or less, preferably about 0.5 to 5 moles, per mole of the 2-halo-2-fluorocyclopropanecarboxylic acid of formula [II].

According to the process of the present invention, the desired 2-fluorocyclopropanecarboxylic acid of formula [I] can be obtained by the simple procedure of developing the Raney nickel alloy in a reaction system containing the 2-halo-2-fluorocyclopropanecarboxylic acid of formula [II]. The mechanism of the reaction remains to be elucidated, but presumably the 2-halo-2-fluorocyclopropanecarboxylic acid of formula [II] in the system is efficiently reduced by active hydrogen produced during the development.

The development or reduction mentioned above can be carried out in various manners, for example, by dissolving the starting 2-halo-2-fluorocyclopropane-carboxylic acid of formula [II] in an aqueous solution of an inorganic base with stirring, adding a Raney nickel alloy and further adding an inorganic base. The ammonia and/or organic base may be added to the system at any stage, whereby the reaction is accelerated. The carboxylic acid of formula [II], Raney nickel alloy, aqueous solution of the inorganic base and ammonia and/or the organic base can be added in any order without specific limitation.

The temperature for the development of the Raney nickel alloy is usually about 0° to 100° C., preferably about 20° to 90° C. The development or reduction requires about 1 to 50 hours, and generally is carried out preferably under atmospheric pressure.

When the starting materials are added at a relatively low temperature, for example at 40° C. or less, the reduction can be accelerated by heating the mixture at a higher temperature, for example at 50° C. or more.

After addition of the starting materials, hydrogen may be fed under atmospheric pressure or under pressure, when necessary. However, the reduction sufficiently proceeds without feeding hydrogen.

The above reduction provides the desired 2-fluorocyclopropanecarboxylic acid of formula [I] in the form of a salt with the base.

After completion of the reaction, the desired 2-fluorocyclopropanecarboxylic acid of formula [I] can be collected, for example, by filtering off the Raney nickel catalyst formed by the development from the reaction mixture, acidifying the filtrate, extracting the acidified filtrate with an organic solvent, and evaporating the low-boiling contents such as the organic solvent and the like from the organic layer.

The pH of the reaction mixture to be adjusted by the acidification is not specifically limited insofar as the pH value is sufficient for forming a free carboxylic acid from the obtained salt. Generally, however, it is preferable to adjust the pH to about 2 or less.

The organic solvent to be used for extraction is not limited specifically and can be selected from a wide range. Examples are ether solvents such as diethyl ether, diisopropyl ether, methyl t-butyl ether and the like, hydrocarbon solvents such as toluene, xylene and the like, halogenated hydrocarbon solvents such as methylene chloride, chlorobenzene and the like, ester solvents such as ethyl acetate and the like, ketone solvents such as methyl isobutyl ketone and the like, etc., among which the ether solvents are preferably used.

When necessary, the desired product thus obtained can be further purified by a conventional method such as distillation, recrystallization, column chromatography or the like. Each of the cis- and trans-2-fluorocyclopropanecarboxylic acid isomers can be isolated by rectification.

Thus, according to the present invention, the desired 2-fluorocyclopropanecarboxylic acid of formula [I] can be produced by the simple procedure of developing a Raney nickel alloy in the presence of the starting 2-halo-2-fluorocyclopropanecarboxylic acid of formula [II] without preparing the Raney nickel catalyst before carrying out the reduction.

Moreover, the process of the present invention is very advantageous for industrial purposes since the desired product can be obtained without feeding hydrogen.

Process (ii)

Process (ii) of the present invention is described below in detail wherein the 2-halo-2-fluorocyclopropanecarboxylic acid of formula [II] is reduced in an aqueous solvent using a Raney nickel catalyst.

Process (ii) of the invention is characterized in that the 2-halo-2-fluorocyclopropanecarboxylic acid of formula [II] is reduced in an aqueous solvent using a Raney nickel catalyst. The Raney nickel catalyst may be one prepared by developing a Raney nickel alloy by a conventional method or one commercially available.

The Raney nickel catalyst for use in the present invention usually contain about 50% by weight of water. The amount of Raney nickel catalyst is usually about 0.025 to 2.5 parts by weight, preferably about 0.05 to 0.75 part by weight, more preferably about 0.05 to 0.5 part by weight (calculated as dry weight), per part by weight of the 2-halo-2-fluorocyclopropanecarboxylic acid [II]. Said catalyst is used preferably in a small amount in view of filtration amenability, since the catalyst is not sufficiently amenable to filtration and thus it requires a long period of time to filter the catalyst from the reaction mixture after completion of the reaction. According to the present invention, the reaction sufficiently proceeds using 0.5 part by weight or less (calculated as dry weight) of the catalyst per part by weight of the 2-halo-2-fluorocyclopropanecarboxylic acid of formula [II].

The reduction is carried out using water as a solvent. The solvent may contain, in addition to water, organic solvents such as alcohols such as methanol, ethanol and the like, esters such as ethyl acetate and the like, ethers such as diethyl ether and the like, etc. In any cases, the amount of water is usually about 1 to 50 parts by weight, preferably about 2 to 30 parts by weight, per part by weight of the 2-halo-2-fluorocyclopropanecarboxylic acid of formula [II]. When using a mixed solvent of water and an alcohol, the amount of the alcohol is not limited specifically but is usually about 1 part by weight or less, preferably about 0.1 part by weight or less, per part by weight of water. When using a mixed solvent of water and an organic solvent other than alcohols, the amount of the organic solvent is preferably about 0.1 part by weight or less per part by weight of water.

The reaction is carried out preferably in the presence of a base, and by doing so, the reaction rate, yield and the like are improved. Such base includes, for example, organic bases such as ethylenediamine and the like, inorganic bases such as alkali metal hydroxides, including sodium hydroxide, potassium hydroxide and the like, etc. Generally, it is preferable to use an organic base in combination with an inorganic base.

When using the base, the amount of the organic base is usually 10 moles or less, preferably about 0.5 to 5 moles, per mole of the 2-halo-2-fluorocyclopropanecarboxylic acid of formula [II], while the amount of the inorganic base is usually about 20 moles or less, preferably about 0.5 to 20 moles, more preferably about 1 to 10 moles, per mole of the 2-halo-2-fluorocyclopropanecarboxylic acid of formula [II].

The reduction is carried out usually at about 0° to 100° C., preferably about 20° to 90° C., under hydrogen pressure of usually about 1 to 100 kg/cm$^2$·G, preferably about 1 to 50 kg/cm$^2$·G. The reaction time is usually about 0.5 to 50 hours.

Process (ii) of the present invention can be carried out in various manners. Generally, however, it is preferable to carry out the reaction, for example, by the following method.

Thus, a pressure-resistant reactor such as an autoclave is charged with the starting material, i.e., the 2-halo-2-fluorocyclopropanecarboxylic acid of formula [II], water, the Raney nickel catalyst and the base, and the mixture was subjected to reaction under pressure of hydrogen.

The 2-halo-2-fluorocyclopropanecarboxylic acid of formula [II], water and the base may be placed into the reactor separately, or the 2-halo-2-fluorocyclopropane-carboxylic acid of formula [II] may be dissolved in water or in an aqueous solution of the inorganic base and then placed into the reactor.

When the 2-halo-2-fluorocyclopropanecarboxylic acid of formula [II] is first dissolved in the aqueous solution of the inorganic base, the concentration of the aqueous solution of the inorganic base can be selected from a wide range, for example, from such a range that the amount of the inorganic base is as specified above. Generally, however, a concentration of about 5 to 35% by weight can be employed.

Alternatively, a mixture of an aqueous solution of the inorganic base having a suitable concentration or water and the 2-halo-2-fluorocyclopropanecarboxylic acid of formula [II] is prepared and placed into the reactor, and the base is placed into the reactor in an additional manner.

Further, all the necessary amount of the organic base and/or inorganic base may be placed into the reactor before starting the reaction, or alternatively the base may be added continuously or intermittently from the start of the reaction until the completion of the reaction.

It is a matter of course that the reaction can be carried out otherwise.

When using the base, the desired 2-fluorocyclopropanecarboxylic acid of formula [I] is usually produced in the form of a salt with the base.

After completion of the reaction, the desired 2-fluorocyclopropanecarboxylic acid of formula [I] can be collected, for example, by filtering off the Raney nickel catalyst from the reaction mixture, acidifying the filtrate when necessary, subjecting the filtrate as such or the acidified filtrate to extraction with an organic solvent, and distilling off the low-boiling contents such as the organic solvent and the like from the organic layer.

The pH of the reaction system to be adjusted by the acidification is not limited specifically insofar as the pH value is sufficient for forming a free carboxylic acid from the obtained salt. Generally, however, it is preferable to adjust the pH to about 2 or less.

The organic solvent for extraction is not limited specifically and can be selected from a wide range. Examples are ether solvents such as diethyl ether, diisopropyl ether, methyl t-butyl ether and the like, hydrocarbon solvents such as toluene, xylene and the like, halogenated hydrocarbon solvents such as methylene chloride, chlorobenzene and the like, ester solvents such as ethyl acetate and the like, ketone solvents such as methyl isobutyl ketone and the like, etc., among which the ether solvents are preferably used.

When necessary, the desired product thus obtained can be further purified by conventional methods such as distillation, recrystallization, column chromatography or the like. Each of the cis- and trans-2-fluorocyclopropanecarboxylic acid isomers can be isolated by rectification.

Thus, according to the present invention, the desired 2-fluorocyclopropanecarboxylic acid of formula [I] can be easily produced in a high yield by reducing the starting 2-halo-2-fluorocyclopropanecarboxylic acid of formula [II] in an aqueous solvent using a Raney nickel catalyst. Moreover, according to the invention, the catalyst can be easily removed from the reaction mass, since only a small amount of the catalyst is required to efficiently produce the desired product of formula [I].

EXAMPLES

The following Examples illustrate the present invention in further detail but are in no way limitative of the scope of the invention. In the Examples, cis and trans indicate the configuration of the fluorine atom and carboxyl group on the cyclopropane ring, and "cis/trans ratio" is intended to mean the molar ratio of the cis isomer to the trans isomer. In the Examples, "%" regarding amounts and concentrations means "% by weight".

In Examples 1 to 9, the 2-halo-2-fluorocyclopropanecarboxylic acid of formula [II] was reduced by developing a Raney nickel alloy in the presence of said carboxylic acid.

Example 1

Two grams of a Raney nickel alloy (containing 50% by weight of nickel) was added with stirring to a solution of 4 g of 2-chloro-2-fluorocyclopropanecarboxylic acid (cis/trans=1.25/1) in 21.2 g of a 5.7% aqueous solution of sodium hydroxide, and the mixture was heated to 35° C. While maintaining the mixture at 30° to 40° C., 20 g of a 20% aqueous solution of sodium hydroxide and 8.7 g of ethylenediamine were added over a period of 30 minutes.

The mixture was stirred for 7 hours while maintaining the reaction system at 30° to 40° C., and then the Raney nickel catalyst was filtered off. The filtrate was acidified (pH=1) by addition of hydrochloric acid and subjected to extraction with methyl t-butyl ether. The organic layer was dried over anhydrous magnesium sulfate and filtered, and the low-boiling contents (the extraction solvent and the like) were distilled off, giving 2.92 g of the desired 2-fluorocyclopropanecarboxylic acid.

The obtained product was analyzed by gas chromatography. As a result, it was found that the conversion was 99.5%, the purity 94.9%, the yield 92.4%, and the cis/trans ratio 1.2/1.

Example 2

The procedure of Example 1 was repeated with the exception that the ethylenediamine was used in an amount of 2.7 g, 4.4 g of a 27% aqueous solution of sodium hydroxide was used in lieu of the 5.7% aqueous solution of sodium hydroxide, 9.6 g of 27% aqueous solution of sodium hydroxide was used in lieu of the 20% aqueous solution of sodium hydroxide, and the stirring while maintaining the reaction system at 30° to 40° C. was continued for 3 hours.

The desired 2-fluorocyclopropanecarboxylic acid thus obtained was analyzed by gas chromatography. As a result, it was found that the conversion was 99.5%, the yield 84.3% and the cis/trans ratio 1.06/1. The aqueous layer separated after the extraction had a green color and contained 0.6% of nickel.

Example 3

The procedure of Example 1 was repeated with the exception that the ethylenediamine was used in an amount of 2.7 g and the stirring while maintaining the reaction system at 30° to 40° C. was continued for 20 hours.

The desired 2-fluorocyclopropanecarboxylic acid thus obtained was analyzed by gas chromatography. As a result, it was found that the conversion was 99.5%, the yield 80.4% and the cis/trans ratio 1.13/1.

Example 4

The procedure of Example 2 was repeated using 4 g of 2-chloro-2-fluorocyclopropanecarboxylic acid (cis/trans= 99/1) in lieu of the carboxylic acid, and the reaction mixture was heated to 50° C. and then stirred for 2 hours while maintaining the reaction mixture at 50° C.

The desired 2-fluorocyclopropanecarboxylic acid thus obtained was analyzed by gas chromatography. As a result, it was found that the conversion was 99.9%, the yield was 99% and the obtained product was a 100% cis-2-fluorocyclopropanecarboxylic acid.

Example 5

A 5.8 g quantity of a Raney nickel alloy (containing 50% by weight of nickel) was added with stirring to 34.5 g of a 39.4% aqueous solution of sodium 2-chloro-2-fluorocyclopropanecarboxylate (cis/trans=1.29/1), followed by heating to 600° C. While maintaining the mixture at 60° to 70° C., a solution of 0.2 g of ethylenediamine in 53.3 g of 28% aqueous ammonia, and 38.3 g of a 45% aqueous solution of sodium hydroxide were added over a period of 4 hours.

Thereafter, the product was isolated by the procedure described in Example 1.

The conversion was 99.9%, the yield was 86.5% and the cis/trans ratio was 1.26/1. The aqueous layer separated after the extraction was colorless and contained 1 ppm or less of nickel.

Example 6

The procedure of Example 5 was repeated with the exception that the Raney nickel alloy was used in an amount of 4.4 g, 53.3 g of 28% aqueous ammonia was used in lieu of the solution of ethylenediamine in 28% aqueous ammonia, and the 45% aqueous solution of sodium hydroxide was used in an amount of 40 g. Subsequently, the product was isolated by the procedure described in Example 1.

The conversion was 99.8%, the yield was 74.8% and the cis/trans ratio was 1.49/1. The aqueous layer separated after the extraction was colorless and contained 1 ppm or less of nickel.

Example 7

A 5.9 g quantity of a Raney nickel alloy (containing 50% by weight of nickel) was added to 32.1 g of a 42.4% aqueous solution of sodium 2-chloro-2-fluorocyclopropanecarboxylate (cis/trans=1.29/1), followed by heating to 40° C. While maintaining the mixture at 40° to 50° C., 26.3 g of 40% aqueous solution of methylamine and 17.3 g of a 45% aqueous solution of sodium hydroxide were added over a period of 4 hours. The mixture was stirred at 40° to 50° C. for 13 hours, and then at 60° to 70° C. for 5 hours, and the product was isolated by the procedure described in Example 1.

The conversion was 97.4%, the yield was 87.4% and the cis/trans ratio was 1.37/1. The aqueous layer separated after the extraction was colorless and contained 1 ppm or less of nickel.

Example 8

Two grams of a Raney nickel alloy (containing 50% by weight of nickel) was added with stirring to 11 g of a 42% aqueous solution of sodium 2-chloro-2-fluorocyclopropanecarboxylate (cis/trans=1.3/1), followed by heating to 35° C. While maintaining the mixture at 35° to 40° C., 8.9 g of ethanolamine and 14.8 g of a 27% aqueous solution of sodium hydroxide were added thereto over a period of 1 hour. The mixture was stirred at 35° to 40° C. for 21 hours, and the product was isolated by the procedure described in Example 1.

The conversion was 98.2%, the yield was 86.8% and the cis/trans ratio was 1.47/1. The aqueous layer separated after the extraction was colorless and contained 1 ppm or less of nickel.

Example 9

The procedure of Example 8 was repeated with the exception that 13 g of 50% aqueous solution of dimethylamine was used in lieu of the ethanolamine, and the stirring of the mixture at 35° to 40° C. was continued for 23 hours instead of 21 hours.

The conversion was 74.5%, the yield was 67.6% and the cis/trans ratio was 2.58/1. The aqueous layer separated after the extraction was colorless and contained 1 ppm or less of nickel.

In Examples 10 to 13, the 2-halo-2-fluorocyclopropanecarboxylic acid of formula [II] was reduced in an aqueous solvent using a Raney nickel catalyst.

Example 10

(a) Two grams of a Raney nickel alloy (containing 50% by weight of nickel) was added to 20 g of water, followed by heating to 35° C. While maintaining the mixture at 30° to 40° C., 20 g of a 20% aqueous solution of sodium hydroxide was added over a period of 20 minutes, and the mixture was stirred for 30 minutes while maintaining the reaction system at 30° to 40° C.

Subsequently, the mixture was washed three times with 20 g of water, giving 2 g of a Raney nickel catalyst (containing about 50% by weight of water). (b) An autoclave was charged with a solution of 2 g of 2-chloro-2-fluorocyclopropanecarboxylic acid (cis/trans=1.17/1) in 21.2 g of a 5.7% aqueous solution of sodium hydroxide, 2 g of the Raney nickel catalyst (containing about 50% by weight of water) obtained in (a) above, 20 g of a 20% aqueous solution of sodium hydroxide and 8.7 g of ethylenediamine. The mixture was reacted under hydrogen pressure of 10 kg/cm$^2$·G at 80° C. for 4 hours.

Subsequently, the Raney nickel catalyst was filtered off, and the filtrate was acidified (pH=1) by addition of hydrochloric acid and subjected to extraction with methyl t-butyl ether. The organic layer was dried over anhydrous magnesium sulfate and filtered, and the low-boiling contents (the extraction solvent and the like) were distilled off, giving 1.29 g of the desired 2-fluorocyclopropanecarboxylic acid.

The obtained product was analyzed by gas chromatography. As a result, it was found that the conversion was 99.8%, the purity 97%, the yield 83% and the cis/trans ratio 1.23/1.

Example 11

An autoclave was charged with a solution of 2 g of 2-chloro-2-fluorocyclopropanecarboxylic acid (cis/trans=1.17/1) in 36 g of water, 2 g of a Raney nickel catalyst prepared in the same manner as in Example 10 (a) (containing about 50% by weight of water) and 8.7 g of ethylenediamine. The mixture was reacted under hydrogen pressure of 20 kg/cm$^2$·G at 80° C. for 20 hours, and the desired 2-fluorocyclopropanecarboxylic acid was isolated by the procedure described in Example 10.

The obtained product was analyzed by gas chromatography. As a result, it was found that the conversion was 78%, the yield 65.1% and the cis/trans ratio 1.57/1.

Example 12

An autoclave was charged with 23 g of 2-chloro-2-fluorocyclopropanecarboxylic acid (cis/trans=1.15/1), 24 g of a 27% aqueous solution of sodium hydroxide, 24 g of a Raney nickel catalyst (NDHT-90 manufactured by Kawaken Fine Chemical Co., Ltd., containing 50% by weight of water and 5% by weight of aluminum), 20 g of water and 30 g of ethylenediamine. The mixture was subjected to reaction under a hydrogen pressure of 10 kg/cm$^2$·G, at 30° to 35° C. for 6 hours.

Subsequently, the desired 2-fluorocyclopropanecarboxylic acid was isolated by the procedure described in Example 10.

The obtained product was analyzed by gas chromatography. As a result, it was found that the conversion was 91%, the yield 79.8% and the cis/trans ratio 1.06/1.

Example 13

An autoclave was charged with 23 g of 2-chloro-2-fluorocyclopropanecarboxylic acid (cis/trans=1.37/1), 24 g of a 27% aqueous solution of sodium hydroxide, 12 g of a Raney nickel catalyst (NDHT-90 manufactured by Kawaken Fine Chemical Co., Ltd., containing 50% by weight of water and 5% by weight of aluminum), 20 g of water and 30 g of ethylenediamine. The mixture was subjected to reaction under a hydrogen pressure of 10 kg/cm$^2$·G at 35° C. for 24 hours. During the reaction, 5 g of ethylenediamine was added 5 hours and 20 hours after starting the reaction.

Subsequently, the desired 2-fluorocyclopropanecarboxylic acid was isolated by the procedure described in Example 10.

The obtained product was analyzed by gas chromatography. As a result, it was found that the conversion was 87%, the yield 81.6% and the cis/trans ratio 1.48/1.

We claim:

1. A process for producing a 2-fluorocyclopropanecarboxylic acid represented by the formula [I]

wherein R is a hydrogen atom or a lower alkyl group comprising subjecting to reduction a 2-halo-2-fluorocyclopropanecarboxylic acid represented by formula [II]

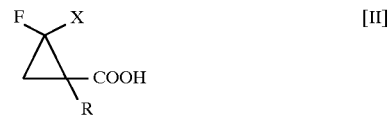

wherein R is as defined above and X is a chlorine atom, a bromine atom or an iodine atom, the reduction being carried out by it developing a Raney nickel alloy in the presence of the 2-halo-2-fluorocyclopropanecarboxylic acid represented by formula [II].

2. The process according to claim 1 wherein the development is carried out by leaching aluminum from the Raney nickel alloy using an inorganic base.

3. The process according to claim 2 wherein the development is carried out by leaching aluminum from the Raney nickel alloy using an inorganic base and additional base.

4. The process according to claim 1 wherein the Raney nickel alloy is used in an amount of 0.05 to 5 parts by weight, per part by weight of the 2-halo-2-fluorocyclopropanecarboxylic acid represented by formula [II].

5. The process according to claim 4 wherein the development is carried out in the presence of water or a mixture of water and alcohols using inorganic base in an amount of 0.1 to 40 parts by weight, per part by weight of the Raney nickel alloy at 0° to 100° C.

6. The process according to claim 3 wherein the additional base is at least one member selected from the group consisting of ammonia and organic bases.

7. The process according to claim 3 wherein the additional base is a mixture of (a) a lower alkylenediamine and (b) at least one member selected from the group consisting of ammonia, lower alkylamines and lower aminoalcohols.

8. The process according to claim 6 wherein the organic base is at least one member selected from the group consisting of lower alkylamines, lower amino alcohols and lower alkylenediamines.

9. The process according to claim 3 wherein the additional base is an organic base.

10. The process according to claim 9 wherein the organic base is ethylenediamine.

11. The process according to claim 6 wherein the additional base is ammonia and at least one of organic bases.

12. The process according to claim 11 wherein the organic base is at least one member selected from the group consisting of lower alkylamines, lower amino alcohols and lower alkylenediamines.

13. The process according to claim 12 wherein the organic base is ethylenediamine.

* * * * *

UNITED STATES PATENT AND TRADEMARK OFFICE
CERTIFICATE OF CORRECTION

PATENT NO. : 5,770,767
DATED : June 23, 1998
INVENTOR(S) : Nobushige ITAYA et al.

It is certified that error appears in the above-identified patent and that said Letters Patent is hereby corrected as shown below:

On the title page, item [54] and column 1, lines 1-3, the title should read as follows:

PROCESS FOR PRODUCING 2-FLUOROCYCLOPROPANECARBOXYLIC ACID

Signed and Sealed this

Twenty-ninth Day of September, 1998

*Attest:*

BRUCE LEHMAN

*Attesting Officer*     *Commissioner of Patents and Trademarks*